US00PP34970P2

(12) United States Plant Patent
Rimland

(10) Patent No.: US PP34,970 P2
(45) Date of Patent: Feb. 7, 2023

(54) ***GEOGENANTHUS* PLANT NAMED 'CF-MKR-GR1'**

(50) Latin Name: *Geogenanthus ciliatus*
Varietal Denomination: CF-MKR-GR1

(71) Applicant: Costa Farms LLC, Miami, FL (US)

(72) Inventor: Michael Kerry Rimland, Miami, FL (US)

(73) Assignee: Costa Farms, LLC, Miami, FL (US)

( * ) Notice: Subject to any disclaimer, the term of this patent is extended or adjusted under 35 U.S.C. 154(b) by 0 days.

(21) Appl. No.: 17/803,489

(22) Filed: Aug. 4, 2022

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Karen M Redden
(74) *Attorney, Agent, or Firm* — Samuel R. McCoy, Jr.

(57) ABSTRACT

'CF-MKR-GR1' is a distinctive *Geogenanthus* plant which is characterized by the combination of a compact growth habit with large, near-orbicular, glossy foliage borne terminally on very dark purple aerial shoots, juvenile and mature foliage with multicolored variegation on both the adaxial and abaxial foliar surfaces, and the uniformity and stability of these characteristics from generation to generation.

4 Drawing Sheets

Latin name of the genus and species: The Latin name of the genus and species of the novel variety disclosed herein is *Geogenanthus ciliatus.*

Variety denomination: The inventive variety of *Geogenanthus* disclosed herein has been given the variety denomination 'CF-MKR-GR1'.

BACKGROUND OF THE INVENTION

Parentage: 'CF-MKR-GR1' is a spontaneous whole-plant mutation which was discovered growing amongst a cultivated population of unnamed *Geogenanthus* sp. plants (not patented) which was discovered by the inventor in August of 2019 at a commercial greenhouse near Miami, Fla. The mutation was first noted for its unique multicolored foliage variegation. At that time, the claimed plant was asexually propagated, and the resulting plants were grown to maturity in order to confirm the distinguishing characteristics first observed and the stability thereof.

Asexual Reproduction: Asexual reproduction of the new cultivar 'CF-MKR-GR1', by way of rooting leaf cuttings, was first performed in September of 2019 at a commercial greenhouse near Miami, Fla. Through five subsequent generations, the unique features of this cultivar have proven to be stable and true to type.

SUMMARY OF THE INVENTION

The cultivar 'CF-MKR-GR1' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'CF-MKR-GR1'. These characteristics in combination distinguish 'CF-MKR-GR1' as a new and distinct *Geogenanthus* cultivar:

1. *Geogenanthus* 'CF-MKR-GR1' exhibits a compact growth habit with a flattened globular plant profile; and
2. *Geogenanthus* 'CF-MKR-GR1' exhibits relatively large, near-orbicular, glossy foliage borne terminally on very dark purple aerial shoots; and
3. *Geogenanthus* 'CF-MKR-GR1' exhibits multi-colored, variegated foliage with irregular streaks of color on the adaxial surface of both the juvenile and mature foliage which range from in between yellow-green and black, yellow-green, red-purple, and greyed-orange; and
4. *Geogenanthus* 'CF-MKR-GR1' exhibits juvenile and mature foliage with a variegated abaxial surface which is colored with irregular streaks of very dark purple, in between. purple and black, and dark red-purple.

BOTANICAL DESCRIPTION OF THE PLANT

Figure 1:
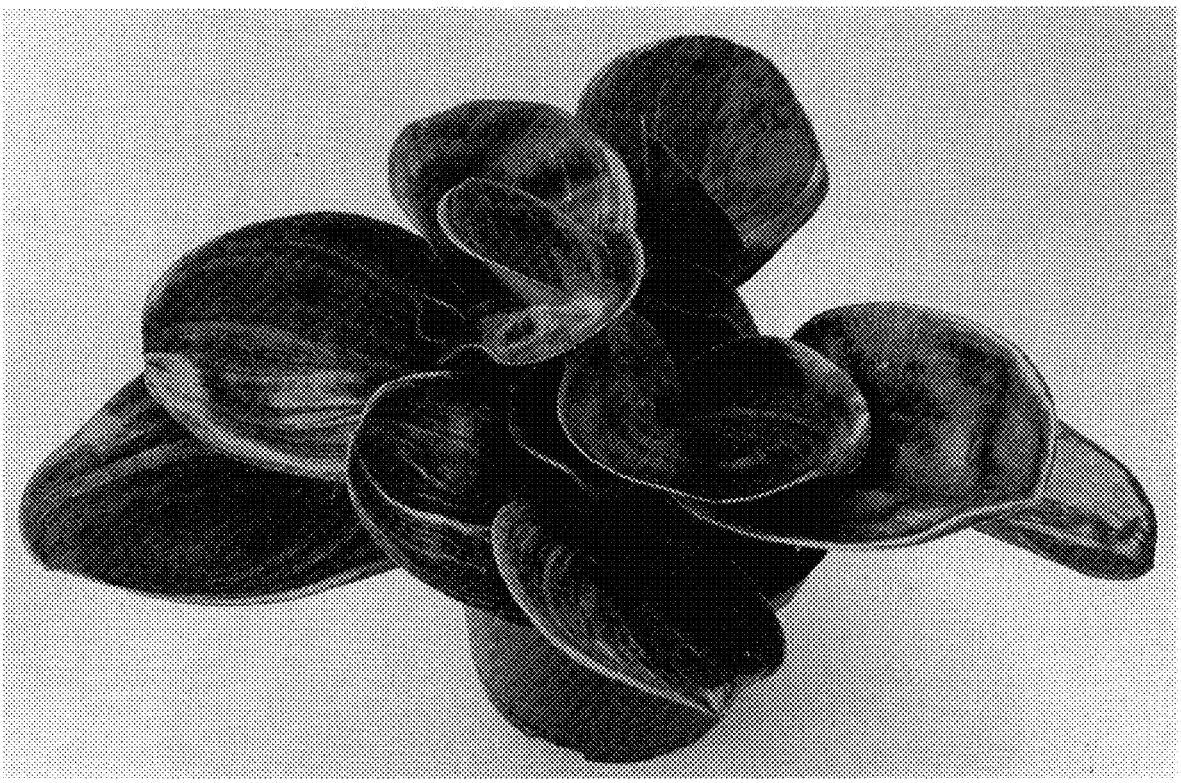
FIG. 1 illustrates, as nearly true as it is reasonably possible to make the same in color photographs of this type, an exemplary plant of 'CF-MKR-GR1' grown in a commercial greenhouse near Miami, Fla. This plant is 9 months old, in a 15 cm container.
Figure 2:
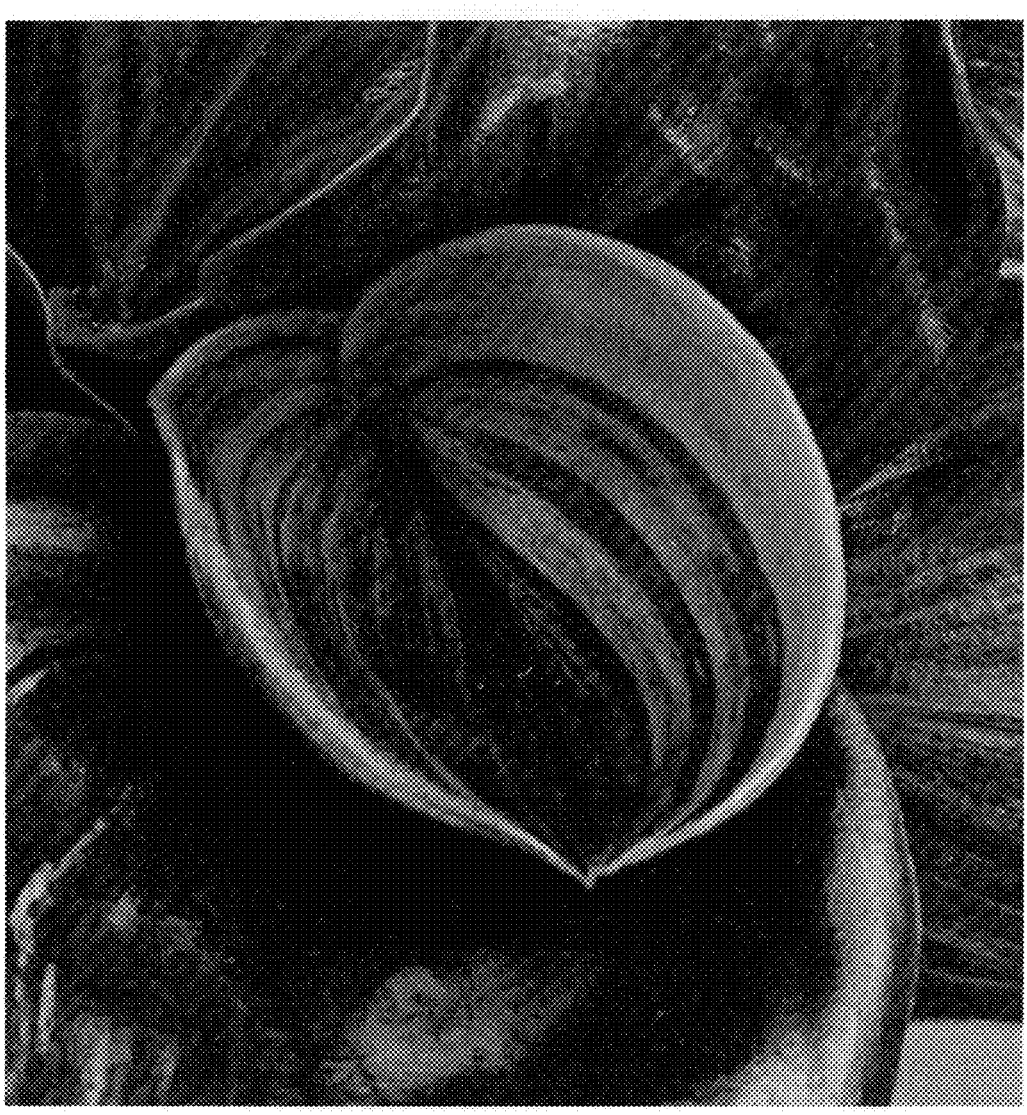
FIG. 2 illustrates, as nearly true as it is reasonably possible to make the same in color photographs of this type, the typical adaxial surface of the juvenile foliage of 'CF-MKR-GR1'.
Figure 3:
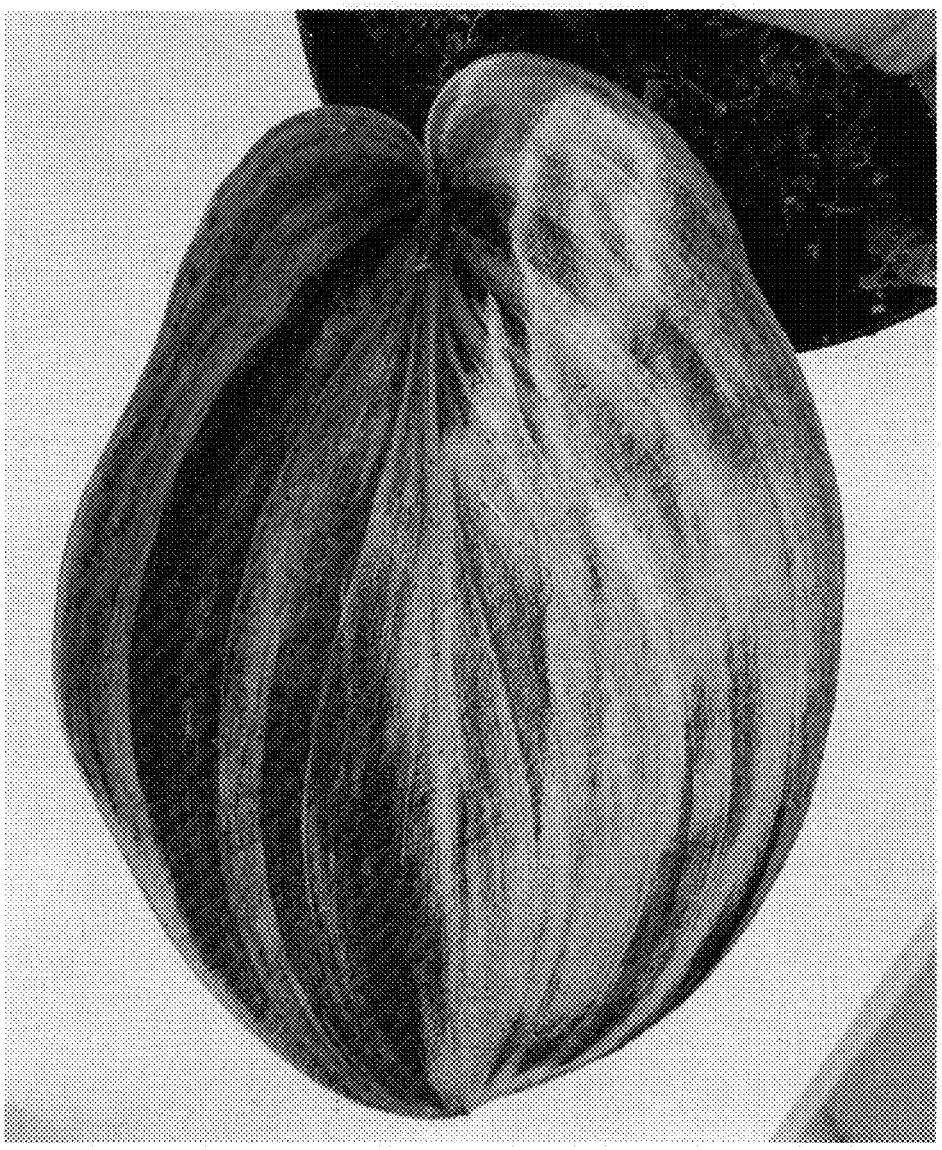
FIG. 3 illustrates, as nearly true as it is reasonably possible to make the same in color photographs of this type, the typical adaxial surface of the mature foliage of 'CF-MKR-GR1'.
Figure 4:
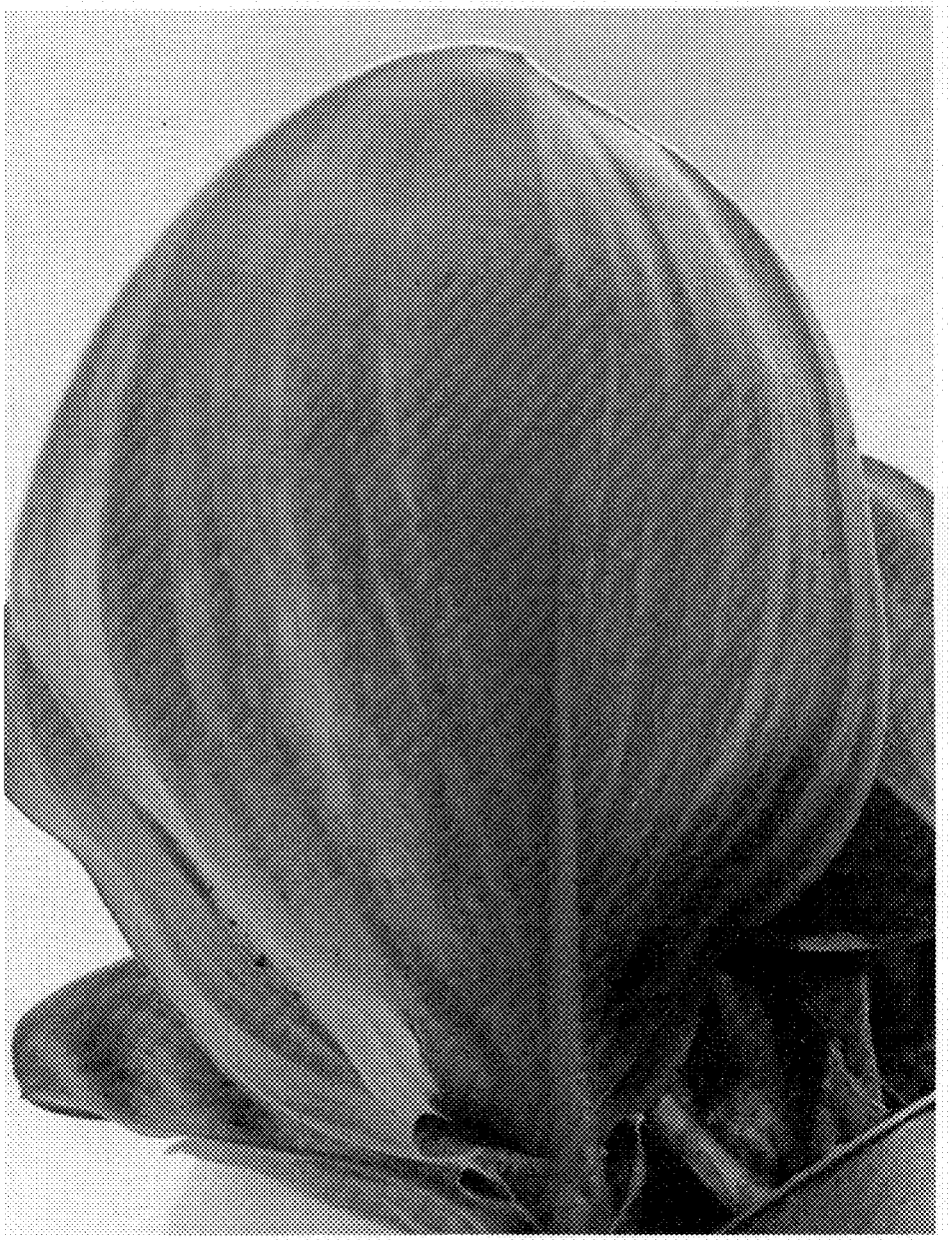
FIG. 4 illustrates, as nearly true as it is reasonably possible to make the same in color photographs of this type, typical abaxial surface of the mature foliage of 'CF-MKR-GR1'.

The following observations and measurements, made in July of 2022, describe a 9-month-old 'CF-MKR-GR1' plant.

The plant was grown from a single unrooted cutting, in 15 cm nursery containers, at a commercial greenhouse near Miami, Fla. The plant was produced using conventional greenhouse production protocols for *Geogenanthus* sp. which entailed growing plants under 80 percent shade, regularly watering with overhead irrigation, and fertilizing with a 180-day slow-release granular fertilizer. No chemical pest measures or photoperiodic treatments were utilized during production.

Those skilled in the art will appreciate that certain characteristics will vary with older or, conversely, with younger plants. 'CF-MKR-GR1' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 1986 (third edition).

A botanical description of 'CF-MKR-GR1' and a comparison with the parent plant is provided below.

Plant description:

*Growth habit*.—Compact herbaceous perennial with short aerial shoots bearing terminal rosettes of foliage.

*Plant shape*.—Flattened globular.

*Height from soil level to top of foliar plane*.—9.0 cm.

*Plant spread*.—29.7 cm.

*Number of basal shoots per plant*.—10.

*Growth rate*.—Moderately slow.

*Propagation*.—Type — Asexual propagation is accomplished by way of stem and leaf cuttings. Time to initiate rooting — Approximately 10 days at 27 degrees Celsius. Time to produce a marketable finished plant — Approximately 6 to 8 months, from an unrooted cutting, at an ambient temperature of approximately 31.5 degrees Celsius to produce a marketable 15 cm container.

*Disease and pest resistance or susceptibility*.—Neither susceptibility nor resistance to pests and diseases common to *Geogenanthus* have been observed.

*Environmental tolerances*.—*Geogenanthus ciliates* is typically marketed as an indoor decorative plant. Tolerates high temperatures but does not tolerate low temperatures or frost; does not tolerate excessive rainfall; low to moderate tolerance to wind; grows best under low light exposure.

Roots:

*General description*.— Exhibits a robust, rhizomatous and tuberous roots system; moderately dense to densely rooted; shallow to moderately deep distribution in the soil profile.

Stems:

*Branching characteristics*.—Short, unbranched aerial shoots arise directly from the soil and bear terminal rosettes of one to two leaves.

*Quantity*.—10 shoots as observed.

*Attitude*.—Varying from nearly vertical to outward at an angle of approximately 30 degrees from horizontal.

*Aspect*.—Round.

*Length*.—3.2 cm, on average.

*Diameter*.—0.7 cm.

*Internode length*.—Indiscernible; foliage is superposed.

*Texture and luster*.—Pubescent and matte.

*Color*.—Nearest to in between purple and greyed-purple, RHS 79A and 183A.

Foliage:

*General*.—Typically with one or two fully developed leaves per shoot, with multiple diminished leaves along the aerial shoots, below the developed foliage.

*Fully developed foliage*.—Arrangement — Foliage borne in terminal rosettes atop the aerial shoots and superposed on the stem. Division — Simple. Attachment — Amplexicaul. Attitude — Nearly horizontal. Shape — Broadly ovate to nearly orbicular. Length — 13.25 cm, on average. Width —11.1 cm, on average. Apex — Obtuse. Base — Amplexicaul to openly-sheathed. Aspect — Concave; margins are very lightly revolute. Margins — Entire; sparsely to moderately ciliate, with small tufts of hairs present at the base of the lamina; slightly undulating. Texture and luster, adaxial surface — Smooth, glabrous and glossy. Texture and luster, abaxial surface — Smooth, puberulent; proximal portion of the midrib is pilose; moderately glossy. Color — Juvenile foliage, adaxial surface — Variegated, with irregular longitudinal streaks of color ranging from in between yellow-green and black (nearest to RHS 147A and 202A), yellow-green (nearest to RHS 147A), red-purple (RHS 59A), red-purple (RHS 60B), greyed-orange (nearest to in between RHS 164A and 167A) which are occasionally suffused with yellow-green (RHS 146A) or greyed-orange (RHS 172B). The composition of the coloration varies from leaf to leaf though the predominant colors observed are red-purple (RHS 59A) and greyed-orange (nearest to in between RHS 164A and 167A). Juvenile foliage, abaxial surface — Variegated, with irregular longitudinal streaks of color ranging from in between purple and black (nearest to RHS 79A and 202A) and red-purple (RHS 71A). Mature foliage, adaxial surface — Variegated, with irregular longitudinal streaks of color ranging from in between yellow-green and black (nearest to RHS 147A and 202A), yellow-green (nearest to RHS 147A), red-purple (RHS 59A), red-purple (RHS 60B), greyed-orange (nearest to in between RHS 164A and 167A) which are occasionally suffused with yellow-green (RHS 146A) or greyed-orange (RHS 172B). The composition of the coloration varies from leaf to leaf though the predominant color observed is in between yellow-green and black (nearest to RHS 147A and 202A). Mature foliage, abaxial surface — Variegated, with irregular longitudinal streaks of color ranging from in between purple and black (nearest to RHS 79A and 202A) and red-purple (RHS 71A). Venation — Pattern — Arcuate. Color, adaxial surfaces — Main veins are colored red-purple, nearest to RHS 61A, proximally, and are indistinguishable along the distal portion of the main vein. The lateral veins are indistinguishable from the surrounding lamina. Color, abaxial surface — Main veins are colored red-purple, nearest to RHS 61A. The lateral veins are indistinguishable from the surrounding lamina.

*Lamina of diminished foliage.*—Arrangement — Whorled. Division — Simple. Attachment — Sheathed. Attitude — Varying from adpressed to outward. Shape — Deltoid. Length — 1.9 cm, on average. Width — 1.1 cm, on average. Apex — Broad acute. Base — Openly-sheathed. Aspect — Concave. Margins — Entire and moderately ciliate; very slightly undulating. Texture and luster, adaxial surface — Glabrous and very slightly glossy. Texture and luster, abaxial surface — Puberulent and matte. Color, adaxial surface — Yellow-green, nearest to RHS 147A yet darker; distal portion and apex are suffused with dark purple; nearest to in between purple and greyed-purple, RHS 79A and 183A. Color, adaxial surface — Nearest to in between purple and greyed-purple, RHS 79A and 183A. Venation — Not visible.

Inflorescence: To date, 'CF-MKR-GR1' has not flowered.

COMPARISONS WITH THE PARENT PLANT

Plants of the new cultivar 'CF-MKR-GR1' differ from the seed parent, an unnamed *Geogenanthus ciliatus* plant (not patented), in the characteristics described in Table 1 below.

TABLE 1

| Characteristic | 'CF-MKR-GR1' | The parent |
|---|---|---|
| General coloration of the adaxial foliar surface; juvenile foliage. | Multi-colored, variegated foliage with irregular streaks of color ranging from in between yellow-green and black, yellow-green, red-purple, and greyed-orahge. The composition of the coloration varies from leaf to leaf though the predominant colors observed are red-purple and greyed-orange. | Dark green, suffused with purple. |
| General coloration of the adaxial foliar surface; mature foliage. | Multi-colored, variegated foliage with irregular streaks of color ranging from in between yellow-green and black, yellow-green, red-purple, and greyed-orange. The composition of the coloration varies from leaf to leaf though the predominant color observed is very dark green, nearest to in between yellow-green and black. | Dark green, suffused with purple. |
| General coloration of the abaxial foliar surface; juvenile and mature foliage. | Multi-colored, variegated foliage with irregular streaks of very dark purple, in between purple and black, and dark red-purple. | Dark red-purple. |

COMPARISONS WITH THE CLOSEST KNOWN COMMERCIAL COMPARATOR

There are no other named cultivars of *Geogenanthus ciliatus* known to the inventor. Therefore, the parent is also the most similar commercial comparator known to the inventor.

That which is claimed is:

1. A new and distinct variety of *Geogenanthus* plant named 'CF-MKR-GR1', substantially as described and illustrated herein.

* * * * *